(12) United States Patent
Plachta et al.

(10) Patent No.: US 11,541,230 B2
(45) Date of Patent: Jan. 3, 2023

(54) IMPLANTABLE ELECTRIC CONNECTING STRUCTURE BETWEEN AN ELECTRIC IMPLANT AND AN ELECTRIC FEED AND DRAIN LINE STRUCTURE

(71) Applicant: Neuroloop GmbH, Freiburg (DE)

(72) Inventors: Dennis Plachta, Voerstetten (DE); Fabian Kimmig, Freiburg (DE); Tim Boretius, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 431 days.

(21) Appl. No.: 16/620,695

(22) PCT Filed: May 28, 2018

(86) PCT No.: PCT/EP2018/063864
§ 371 (c)(1),
(2) Date: Dec. 9, 2019

(87) PCT Pub. No.: WO2018/224341
PCT Pub. Date: Dec. 13, 2018

(65) Prior Publication Data
US 2020/0246609 A1    Aug. 6, 2020

(30) Foreign Application Priority Data

Jun. 9, 2017  (DE) .................... 10 2017 209 773.6

(51) Int. Cl.
*A61N 1/05* (2006.01)
*H01R 13/24* (2006.01)
*H01R 13/58* (2006.01)

(52) U.S. Cl.
CPC ........... *A61N 1/05* (2013.01); *H01R 13/2464* (2013.01); *H01R 13/5829* (2013.01)

(58) Field of Classification Search
CPC ............ H01R 13/2464; H01R 13/5829; H01R 2201/12; A61N 1/05; A61N 1/3752;
(Continued)

(56) References Cited

U.S. PATENT DOCUMENTS

| 5,324,322 A | 6/1994 | Grill, Jr. et al. |
| 8,788,064 B2 * | 7/2014 | Mercanzini ............ A61B 17/34 |
| | | 607/45 |

(Continued)

FOREIGN PATENT DOCUMENTS

WO    2016055512 A1    4/2016

OTHER PUBLICATIONS

International Search Report for PCT/EP2018/063864, dated Aug. 9, 2018; English translation submitted herewith (5 pgs.).

*Primary Examiner* — Vanessa Girardi
(74) *Attorney, Agent, or Firm* — Fitch, Even, Tabin & Flannery LLP

(57) ABSTRACT

The invention is an implantable electrical connection between an electrical implant which has at least one electrical conductor and at least one electrical feed line. The invention further relates to a method for producing an implantable electrical connection between an electrical implant. The invention comprises at least one electrical cable having a cable end, to which an electrically conductive flat piece is unsupportedly fined, and that the at least one implant-side electrical conductor is joined to the flat piece.

15 Claims, 2 Drawing Sheets

(58) Field of Classification Search
CPC .... A61N 1/3754; A61N 1/3758; A61N 1/378; A61N 1/3787; A61B 2562/225
See application file for complete search history.

(56) References Cited

U.S. PATENT DOCUMENTS

| | | | | |
|---|---|---|---|---|
| 8,968,331 | B1* | 3/2015 | Sochor | A61B 17/3468 606/129 |
| 2004/0176831 | A1* | 9/2004 | Gliner | A61N 1/0531 607/142 |
| 2017/0361110 | A1* | 12/2017 | Stouffer | A61N 1/37229 |
| 2020/0155857 | A1* | 5/2020 | Lu | H05K 1/0271 |

* cited by examiner

IMPLANTABLE ELECTRIC CONNECTING STRUCTURE BETWEEN AN ELECTRIC IMPLANT AND AN ELECTRIC FEED AND DRAIN LINE STRUCTURE

CROSS REFERENCE TO RELATED APPLICATION

Reference is made to PCT/EP2018/063863 filed May 28, 2018, designating the United States, which claims priority to German Application No. 10 2017 209 767.1 filed Jun. 9, 2017, which are incorporated herein by reference in their entirety

BACKGROUND OF THE INVENTION

Field of the Invention

The invention relates to an implantable electrical, connecting structure between an electrical implant, which has at least one electrical conductor, and an electric feed and drain line structure.

Description of the Prior Art

Electronic implants, which are suitable for permanent, or at least long-term, retention in the body, are typically used to influence organ functions therapeutically. Examples of known art are cardiac or brain pacemakers. Depending on the application purpose and complexity of the therapeutic objective, generic implants have a multiplicity of electrical feed and drain lines, which supply the implant in question with electrical control and regulatory signals, together with electrical power. The number of electrical feed and drain lines for electronically complex implants may well include twenty or more electrical lines assembled into a flexible cable by which the implant is connected to a control unit, which is usually combined with a power source. The intracorporeal positioning of the control unit and the power source is usually performed subcutaneously in a part of the body, such as the chest region, or near the clavicle, where the external and internal stresses caused by movement are as small as possible for the person, and ease of surgical access is possible.

As a rule, the electrical feed and drain lines between the implant and at least one of the control unit and the power source are not integrally designed, but are implemented via at least one interface by an intra-corporeal plug connection, or a detachable or non-detachable electrical connection, for example a bonded or soldered connection. On the one hand, this raises problems related to the installation space required for the interface, and on the other hand it is necessary to make the interface region moisture-resistant, on account of the moist intra-corporeal environment.

Using the example of an implantable cuff electrode to be supplied via a multi-pole feed and drain line structure, the problems existing up to the present time concerning an implantable electrical multi-pole connecting structure that are known per se will be explained in more detail with reference to the illustrations to be found in FIGS. 2a to 2c.

FIGS. 2a-c show a prior art electrical implant cuff electrode 1 designed as a winding electrode for enclosing a nerve fiber bundle 2. For the purpose of therapeutic stimulation of the nerve fiber bundle 2, the cuff electrode 1 provides a large number of individual electrode surfaces, which are each supplied separately with electrical power and control signals. For this purpose, the multiplicity of individual electrical feed and drain lines 3 run inside a flexible, planar support substrate 4, which is formed as a polymer film. The numerous electrical feed and drain lines 3 end formed as an end face connection of a so-called electrically conductive microflex structures 5, which are arranged side-by-side, as shown in detail in FIG. 2b, to which individual electrical contacts must be made.

For the purpose of making electrical contact with the microflex structures 5, a ceramic adapter plate 6 is used in a known manner which, in accordance with the number and arrangement of the microflex structures 5, (so-called microflex contacts or microflex pads 7) are attached which are brought into contact with the microflex structures 5, which in each case are connected individually in an electrical connection to the electrode surfaces 8 mounted on the surface of the ceramic adapter plate 6. Individual electric wires 10 of an electrical feed and drain line structure 11 are connected to the individual electrode surfaces 8, designed as solder pads, via soldered or bonded connections 9.

FIG. 2c shows a schematic longitudinal section through the ceramic adapter plate 6 illustrated in FIG. 2b, on which the electrical connections V1, V2 between the implant-side electrical leads 3 on the one hand, and the wires 10 leading into the electric feed and drain line structure 11 on the other hand, are shown in detail. The wires 10 make electrical contact by a soldered or bonded connection 9 to the electrode surfaces 8 provided on the ceramic adapter plate 6. The electrode surfaces 8 in turn are individually connected to electrical conductor structures 12 mounted on the ceramic adapter plate 6, which are preferably platinum/gold conductor tracks. A microflex contact 13 is used for the electrical connection V2 of the respective implant-side electrical feed and drain leads 3 to the electrical connecting structures 12 mounted on the ceramic adapter plate 6. For this purpose, the support substrate 4 is formed as a polymer film within which the individual electrical feed and drain leads 3 are embedded, which in each case has an opening 14 passing through the support substrate 4, and also the respective electrical feed and drain lead 3, into which opening 14 a ball bond 15, preferably of gold, is introduced.

In order to improve the electrical as well as the mechanical contact between an electrical feed and drain line 3 and the electrical conductor 12 mounted on the ceramic adapter plate, two, three or more of such microflex contacts 13 can be provided side-by-side along the electrical feed and drain line 3 running within the support substrate 4, in a manner known per se.

The entire electrical connection arrangement shown in FIGS. 2b and 2c is covered by a biocompatible plastic, to be as impermeable as possible.

It is obvious that the installation space required for the electrical connecting structure of known art increases with the increased complexity and multi-polarity of the unit to be implanted. As a result the loading on and irritation to the patient also increases in the same manner.

An implantable thin-film electrode arrangement, which has a uniform thin-film surface substrate, which has a first section that can be deformed into a winding electrode, a second section for making electrical contact with an electric feed and drain line structure, and a third section connecting the two sections with one another, is discussed in U.S. Pat. No. 5,324,322. In this patent nothing is presented concerning the configuration of the contact ends in terms of the electrical feed and drain line structure.

SUMMARY OF THE INVENTION

The invention is an implantable electrical connection between an electrical implant, which has at least one electrical conductor, and electrical feed and drain lines, which significantly reduces the loading on the patient, compared to generic connecting structures of the known art. In particular, a connection is created that is flexible for ensuring a high degree of reliability regarding a desired durable electrical connection.

The implantable electrical connection of the invention is between an electrical implant, which has at least one electrical conductor, and an electrical feed and a drain line, in which the electrical feed and drain line comprises at least one electric cable with a cable end to which an electrically conductive flat piece is attached in an unsupported manner to the flat piece to which the at least one implant-side electrical conductor is directly joined.

The connection of the invention avoids having the rigid and planar ceramic adapter plate, and provides the possibility of a highly flexible configuration of the implantable electrical connecting structure of a miniaturizable design, by which a patient-specific loading associated with the implantation can be significantly reduced.

The invention is based on the connecting the end of an implant-side electrical conductor directly to the end of a cable, which is part of an electrical feed line and a drain line, and, for example, is electrically connected to at least one of an electrical energy and control module. The electrical connection is robust and mechanically loadable, such that it can withstand compressive and tensile forces resulting from elastic or plastic deformations of the cable section immediately adjacent to the connection, or of the implant-side electrical conductor. In order to achieve the high degree of flexibility, the flat piece attached to the cable end is unsupported by any kind of mechanical support, and defines the electrical and mechanical connection region between an implant-side electrical conductor and a cable.

The flat piece preferably is the same metallic material as the cable itself, can be a separate component that is permanently attached to the cable end by a joint, for example by soldering, welding, adhesive or mechanical clamping.

The size and shape of the flat piece, which is preferably designed as a metallic platelet, has been selected to miniaturize the implantable electric connecting structure as far as possible, exclusively for the purpose of providing a mechanically strong and electrically conductive connection between one cable end of the electrical feed and drain line structure and one implant-side electrical conductor, having surface sizes measuring in the range of only a few $\mu m^2$.

At the same time, it is appropriate to form the flat piece by same material as the cable material at the cable end so that the flat piece is integrally connected to the respective cable.

The support substrate, which is a flexible film electrically non-conductive surface element which confers to the electrical conductors embedded in the film surface element both a defined relative arrangement to one another, and also a mechanical hold for their handling as a whole. In a particularly preferred embodiment, the film support substrate has finger shaped film end sections for making electrical contact with the individual electrical conductors in an edge-side film region, along each of which at least one electrical conductor is embedded. In each of the finger film end sections at least one opening is provided, which passes through the film together with the at least one electrical conductor and within which the at least one electrical conductor has a freely accessible conductor surface, which is electrically and mechanically robustly connected to a flat piece of a cable by one of a welded, adhesively bonded, wire bonded, ball bonded or soldered connection.

The joining of a flat piece attached to one cable end to the exposed electrical conductor ends in the finger film end sections requires only a mutual spatial overlapping and joining, preferably by forming a local microflex contact. In order to improve the electrical and mechanical contact between an electrical conductor and a flat piece, microflex contacts can be provided along one conductor end.

By virtue of the spatially separated formation of the electrical contacts between the cables and the electrical conductors, that preferably has only one cable lead per each finger film end section. The cables can be arranged spatially independently of one another, for example in order to bring them together to form the slimmest possible cable loom, and the finger film end sections can also be wound or rolled together, in the context of film flexibility, to form the most compact and space-saving film geometry possible.

The implantable electrical connecting structure of the invention can be produced in a particularly advantageous way. Thus, first of all it is necessary to provide at least one cable of the electrical feed line and drain line, with an electrically conductive flat piece attached to the cable end. Such a pre-assembled cable can be provided either by joining a separate metallic flat piece to a cable end, or by mechanically deforming a cable end to form a flat piece integrally connected to the cable end.

In addition, the flat piece attached to the cable end is joined to a freely accessible end section of an implant-side electrical conductor. The handling of the cable and the electrical conductor during the joining process, in which a welding, adhesive bonding, wire bonding, ball bonding or soldering technique is preferably used, is simplified by the mechanically stable connection of the at least one electrical conductor within the flexible, film, electrically non-conductive surface element, which is positioned in a fixed manner on a base. Thus, it is only necessary to position the cable-side flat piece at the location of the exposed conductor end section, preferably between the support and the flat piece. For example, by applying a gold ball bond in the region of the finger film end sections together with openings through the electrical conductor end sections creates a stable microflex contact.

BRIEF DESCRIPTION OF THE DRAWINGS

The drawings illustrate a preferred form of embodiment of an implantable electric connection designed according to the invention. Finally, a polymeric encapsulation material is preferably applied around the electrical connecting structure to protect the electrical connection from the aqueous environment of the body.

The invention is described below in an exemplary manner by way of examples of embodiment with reference to the drawings, without any limitation of the general inventive concept.

FIG. 1b shows a longitudinal section through a microflex contact in accordance with FIG. 1a.

DETAILED DESCRIPTION OF THE INVENTION

Figure 1A:
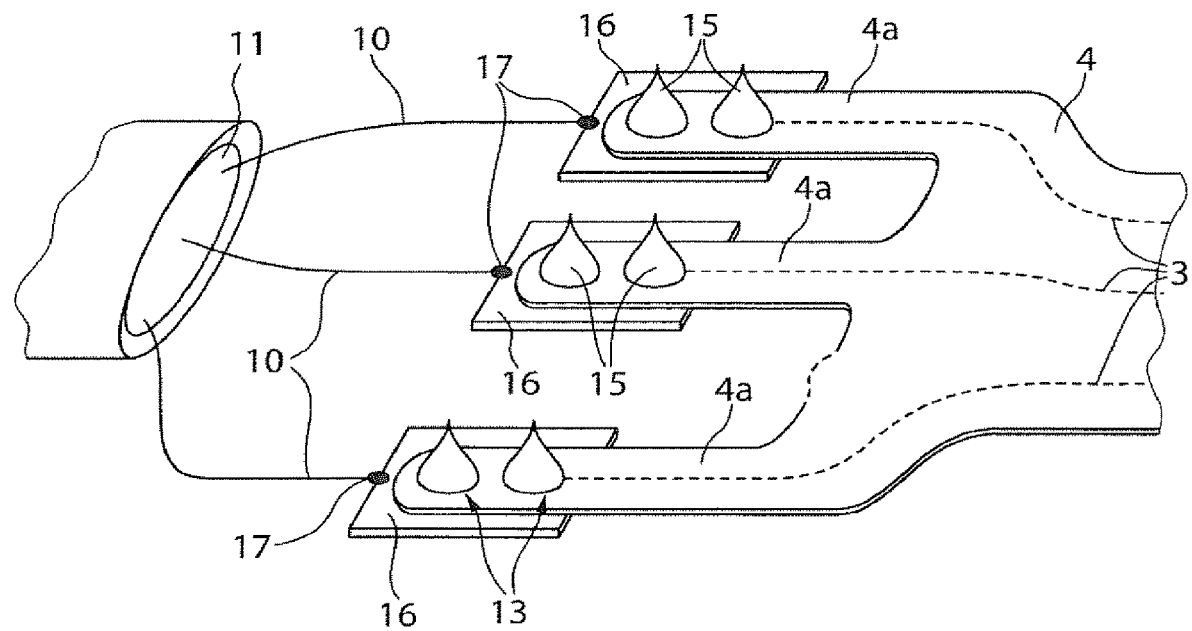
FIG. 1a shows an illustration of the implantable electrical connecting structure in accordance with the invention.

FIG. 1a shows an implantable electrical connection between electric conductors 3 leading to an implant, which correspond in number to the electrical supply cables 10, which are combined into an electrical feed line and drain line 11, and are, for example, connected to an energy supply and control module.

The electrical conductors 3 provided on the implant side are usually integrated in a support substrate 4 which is a flexible, film having an electrically non-conductive surface element 4, preferably of a biocompatible polymer film. In the example embodiment as shown, each individual electrical cable 3 leads along a finger film end section 4a. The number of individual film end sections 4a corresponds to the number of individual electrical lines 3 leading to the implant.

Figure 1B:
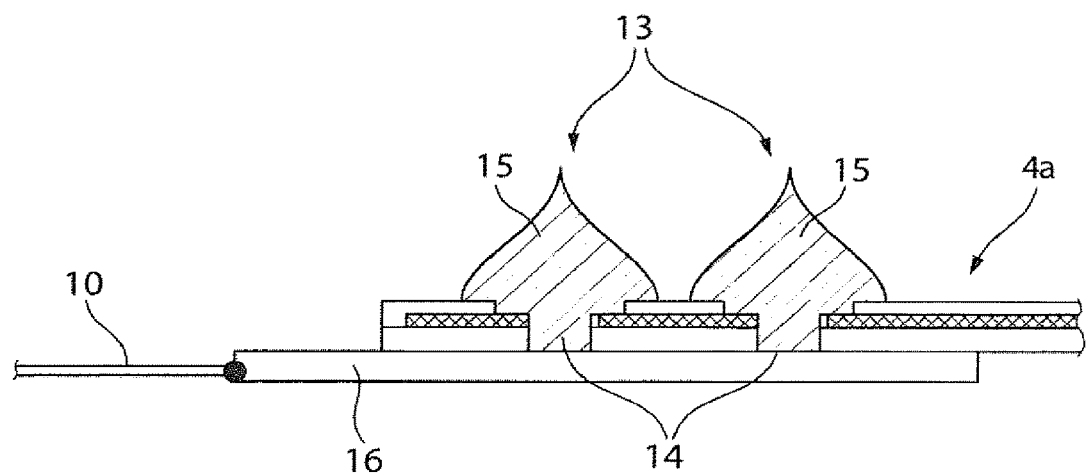
Figure 2A:
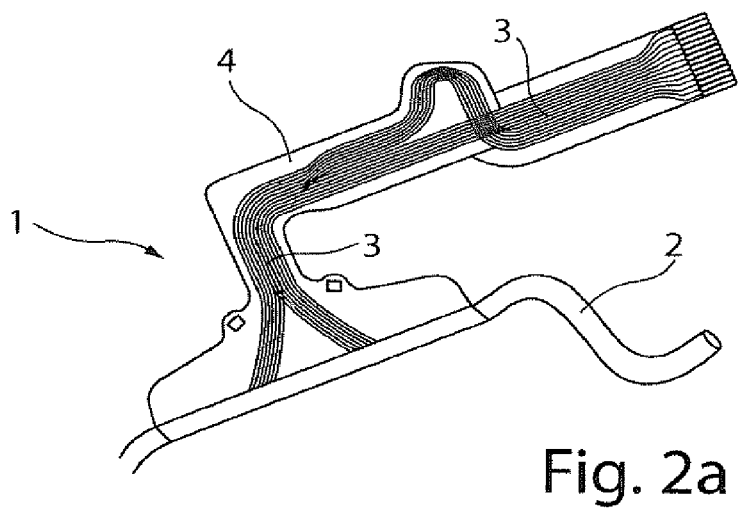
FIGS. 2a, b, c show a prior art implantable connecting structure in accordance with the prior art.
Figure 2B:
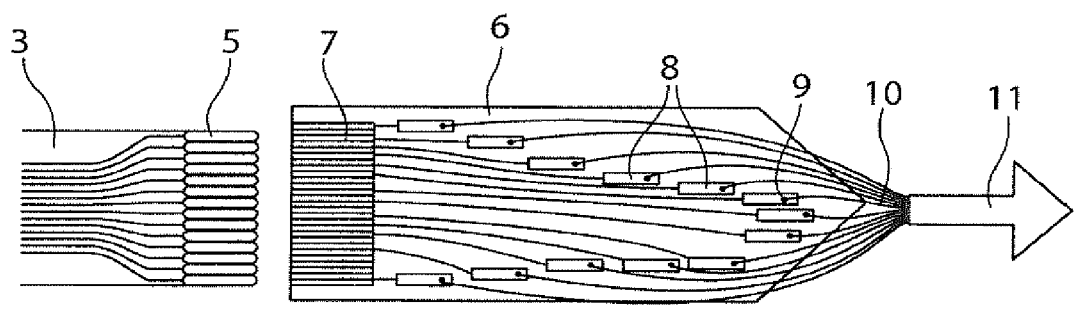
Figure 2C:
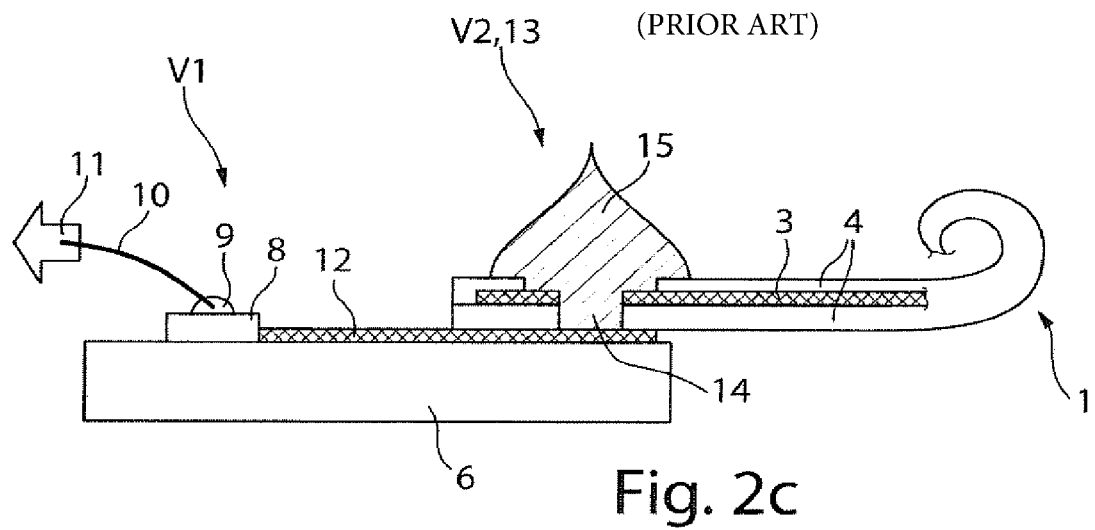

For purposes of making contact between the electrical lines 3 and an electrical supply cable 10, each cable 10 provides a metallic, platelet flat piece 16, which is either connected to the end of a cable 10 via a joint 17, for example by welding, adhesively bonding, wire bonding or a soldered joint, or is integrally formed from the cable end by material deformation. See also the longitudinal section representation in FIG. 1b in terms of a film end section 4a with two microflex contacts 13.

Each of the finger film end sections 4a has two openings 14 formed into two microflex contacts 13, which pass through both the film end section 4a and the electrical conductor 3 locally. Each individual film end section 4a rests directly on one side of a surface of the flat piece 16, and has a thickness ranging from some 10 g of μm to some 100 g of μm. To provide joints that are electrically and mechanically sound, the two openings 14 within each individual film end section 4a are filled with a ball bond 15 which preferably is a gold bond.

If necessary, only one microflex contact 13, or multiple microflex contacts 13, can be provided along an electrical conductor 3, depending on the anticipated loading situation that the connecting structure has to withstand.

The shape and surface size of the individual flat pieces 16 must be selected to be as miniaturized and compact as possible for each individual electrical connecting structure, and is primarily directed at the shape and size of the implant-side film end sections 4a.

Even with a large number of electrical conductors 3 and the cables 10 connected thereto, it is possible to transform the finger film end sections 4a into a small cylindrical design, by winding them, for example, around an axis oriented along the longitudinal extent of the film end sections 4a, from which the cables 10, in close proximity to one another, extend into the electrical feed and drain line structure 11. It is precisely this deformability of the design of the implantable electrical connecting structure that constitutes the particular advantage, by which miniaturization of the structure is made possible.

Other shapes and geometries can also be used for the configuration of the contact region of the film support substrate 4a. All connection techniques known in the art, and suitable for this particular application, such as friction welding, ultrasonic welding, soldering, gluing, bonding methods, etc., are also suitable for the configuration of the electrical and mechanical joint between the individual electrical conductors 3 and the flat pieces 16 of the cables 10.

In order to prevent the electrically conductive flat pieces 16 from forming electrical short circuits, they must be enclosed within an electrically insulating layer material or a potting compound before a space-saving sculpting of the connecting structure.

LIST OF REFERENCE SYMBOLS

1 Cuff electrode arrangement
2 Nerve fiber bundle
3 Electric lines
4 Biocompatible support substrate, polymer film
4a Film end section
5 Microflex structures
6 Ceramic adaptor plate
7 Microflex contacts, microflex pads
8 Electrode surfaces
9 Soldered joint
10 Cable
11 Cable electric feed line and drain line
12 Electric conductor
13 Microflex contact
14 Opening
15 Ball bond, gold bond
16 Flat piece
17 Joint

The invention claimed is:

1. An implantable electrical connecting structure configured for implantation into a patient between an electrical implant and an implantable feed and drain structure, the electrical feed and drain structure including at least two electrical cables each with a cable end, electrically conductive flat pieces, and means for respectively electrically connecting each cable end to a different electrically conductive flat piece and each cable end connected to one of the electrically conductive flat pieces being unsupported when the at least two electrical cables are implanted and being independently moveable to withstand compressive and tensile forces resulting from patient movements after implantation.

2. The implantable electrical connecting structure according to claim 1, wherein each means for connecting comprises at least one of a wire bond, a ball bond or a soldered connection.

3. The implantable electrical connecting structure according to claim 2, wherein at least two electrical conductors are integrated into a flexible film of non-electrically conductive material and each electrical conductor having an accessible end connected to a different respective one of the electrically conductive flat pieces.

4. The implantable electrical connecting structure according to claim 1, wherein each electrically conductive flat piece is metallic.

5. The implantable electrical connecting structure according to claim 4, wherein at least two electrical conductors are integrated into a flexible film of non-electrically conductive material and each electrical conductor having an accessible end connected to a different respective one of the electrically conductive flat pieces.

6. The implantable electrical connecting structure according to claim 4, wherein each means for connecting comprises at least one of a wire bond, a ball bond or a soldered connection.

7. The implantable electrical connecting structure according to claim 6, wherein at least two electrical conductors are integrated into a flexible film of non-electrically conductive material and each electrical conductor having an accessible end connected to a different respective one of the electrically conductive flat pieces.

8. The implantable electrical connecting structure according to claim 1, wherein the electrical conductive flat pieces when attached to the cable end by the means for connecting do not have any mechanical support.

9. The implantable electrical connecting structure according to claim 8, wherein each means for connecting comprises at least one of a wire bond, a ball bond or a soldered connection.

10. The implantable electrical connecting structure according to claim 9, wherein at least two electrical conductors are integrated into a flexible film of non-electrically conductive material and each electrical conductor having an accessible end connected to a different respective one of the electrically conductive flat pieces.

11. The implantable electrical connecting structure according to claim 8, wherein each electrically conductive flat piece is metallic.

12. The implantable electrical connecting structure according to claim 11, wherein at least two electrical conductors are integrated into a flexible film of non-electrically conductive material and each electrical conductor having an accessible end connected to a different respective one of the electrically conductive flat pieces.

13. The implantable electrical connecting structure according to claim 11, wherein each means for connecting comprises at least one of a wire bond, a ball bond or a soldered connection.

14. The implantable electrical connecting structure according to claim 13, wherein at least two electrical conductors are integrated into a flexible film of non-electrically conductive material and each electrical conductor having an accessible end connected to a different respective one of the electrically conductive flat pieces.

15. A method of making an electrical implant and implantable feed and drain structure, the electrical feed and drain structure including at least two electrical cables each with a cable end, electrically conductive flat pieces, and means for respectively electrically connecting each cable end to a different electrically conductive flat piece, and wherein each electrical conductor, means for respectively connecting and connected flat pieces are independently moveable when implanted to withstand compressive and tensile forces resulting from deformations after implantation, the method comprising:

attaching each electrically conductive flat piece to the cable end at one of the means for connecting.

* * * * *